US006007235A

United States Patent [19]

Freud et al.

[11] Patent Number: 6,007,235
[45] Date of Patent: Dec. 28, 1999

[54] SAMPLING AND DILUTING SYSTEM FOR PARTICLE SIZE DISTRIBUTION MEASUREMENT

[75] Inventors: Paul J. Freud, Furlong; Glenn W. Dixon, Jenkintown, both of Pa.

[73] Assignee: Honeywell Inc., Minneapolis, Minn.

[21] Appl. No.: 09/030,465

[22] Filed: Feb. 25, 1998

[51] Int. Cl.[6] .......... B01F 15/02

[52] U.S. Cl. .......... 366/136; 366/138; 366/140; 366/160.2

[58] Field of Search .......... 366/136–138, 366/140, 143, 159.1, 160.1, 160.2, 162.1, 341; 73/863.58, 863.81, 863.83, 863.86; 137/563, 896, 897

[56] References Cited

U.S. PATENT DOCUMENTS

| | | | |
|---|---|---|---|
| 3,414,238 | 12/1968 | Catanzaro | 366/140 |
| 4,470,316 | 9/1984 | Jiskoot | 366/140 |
| 4,494,413 | 1/1985 | Bukkems et al. | 73/863.58 |
| 4,496,244 | 1/1985 | Ludwig | 366/136 |
| 4,720,998 | 1/1988 | Hogue | 366/140 |
| 5,052,425 | 10/1991 | Hohenberg et al. | 73/863.58 |
| 5,416,580 | 5/1995 | Trainer . | |
| 5,439,288 | 8/1995 | Hoffman et al. | 366/137 |
| 5,522,660 | 6/1996 | O'Dougherty et al. | 366/136 |

*Primary Examiner*—Charles E. Cooley
*Attorney, Agent, or Firm*—Anthony Miologos

[57] ABSTRACT

A system is disclosed for the extraction of a representative sample of a processed medium, flowing in a process stream under a first pressure force, and the delivery of the extracted representative sample to a mixing chamber along with a diluent medium. The system includes a source of a second pressure force connected to the mixing chamber, the second pressure force having a value less than the first pressure force of the process stream. An extraction flow control device connects the mixing chamber to the process stream and is operable into a first or alternatively a second position. When operated in the first position the second pressure force of the mixing chamber is connected to the first pressure force of the process stream and, responsive to the pressure force difference, a portion of the processed medium is drawn from the process stream through the extraction flow control device. A source of diluent medium under a third pressure force is further included connected to the extraction flow control device. The third pressure force also has a value greater than the second pressure force. Operating the extraction flow control device into the second position isolates the first pressure force of the process stream from the second pressure force and connects the second pressure force to the third pressure force of the source of diluent medium. Responsive to the pressure force difference between the third pressure force and the second pressure force, diluent medium flows from the source of diluent medium through the extraction flow control device to the mixing chamber, carrying with it the representative sample of processed medium previously extracted.

10 Claims, 1 Drawing Sheet

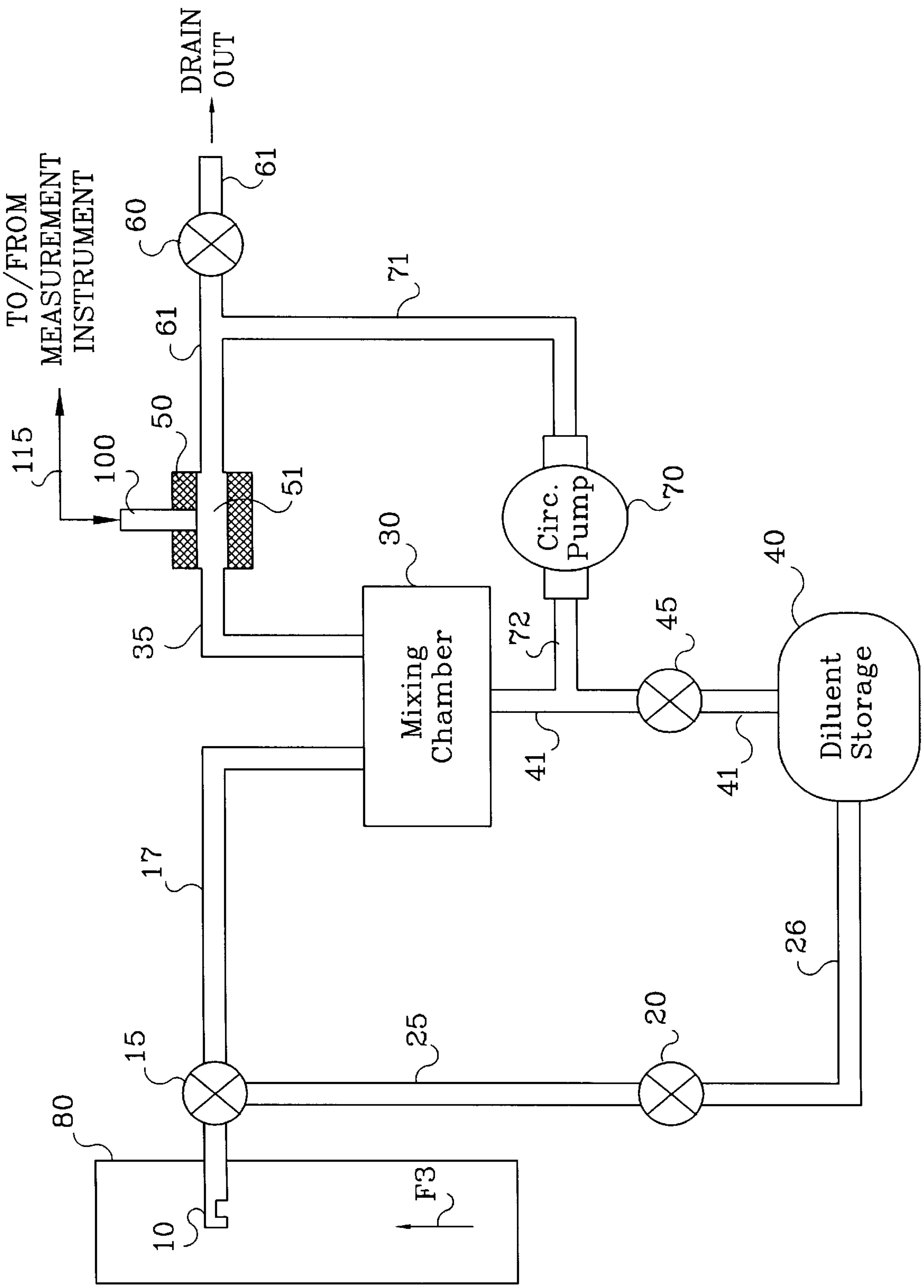
TO/FROM
MEASUREMENT
INSTRUMENT
DRAIN
OUT
115
100
50
51
61
60
61
71
30
35
Mixing
Chamber
72
Circ.
Pump
70
45
40
Diluent
Storage
41
41
17
26
20
25
15
80
10
F3

SAMPLING AND DILUTING SYSTEM FOR PARTICLE SIZE DISTRIBUTION MEASUREMENT

FIELD OF THE INVENTION

This invention relates generally to the field of particle size distribution measurement and more particularly to a sampling and diluting system for extracting and preparing a processed medium for analysis by a particle size distribution measurement instrument.

BACKGROUND OF THE INVENTION

Particle size distribution is an important parameter in many processes and its accurate measurement is required for the precise and cost-effective control of the process. The measurement of particle size distribution in order to accurately control a process finds importance in industries that manufacture cement, cosmetics, pharmaceuticals and the like. A number of instruments are presently used in industry that use angular light scattering or dynamic light scattering techniques to measure particle size distribution in a liquid medium. These instruments analyze and measure the concentration of particles suspended in the liquid medium and provide a measurement that is used to adjust the process in order to correct for any irregularities in the final processed product. One such angular light scattering measurement instrument is taught in U.S. Pat. No. 5,416,580, to Trainer et al, issued May 16, 1995.

In order for these aforementioned instruments to measure correct particle size distribution, a sample representative of the processed medium to be analyzed must be extracted from the process, conditioned and applied to a measurement instrument. Conditioning disperses the particles within the suspension into a concentration value that is within the concentration requirements of the measurement technique being utilized. The concentration of particles within a typical process is generally higher than is allowed by the measurement technique being utilized and the aforementioned conditioning introduces some form of dilution to disperse the concentration. For example, in the case of instruments that employ angular light scattering techniques, multiple scattering limits the concentration to less than 0.1% of particles in suspension. In the case of dynamic light scattering, particle-to-particle interactions limit concentration to less than 3%. Particle concentrations in a processed medium, however, can be as high as 50% by volume.

Current practices utilize a mechanical device to enter the process, capture a sample of the processed medium and withdraw the sample into a dilution chamber. Diluent is pumped by a mechanical device into the dilution chamber to provide the correct ratio of sample to diluent. The now conditioned sample is circulated to the measurement instrument for analysis. Such conditioning methods and associated apparatus are taught in U.S. Pat. No. 4,496,244. to Ludwig et al, issued Jan. 29, 1985, and U.S. Pat. No. 5,439,288, to Hoffman et al, issued Aug. 8, 1995.

The presently known systems suffer from poor reliability and excessive maintenance due to the requirement for multiple seals to effect the mechanical motion of extracting the sample from the process. Additionally, such systems require many hours of maintenance in cleaning the mechanical extraction devices in order to operate efficiently.

SUMMARY OF THE INVENTION

Therefore, there is provided by the present invention a system for the extraction of a representative sample of a processed medium, flowing in a process stream under a first pressure force, and the delivery of the extracted representative sample to a mixing chamber along with a diluent medium. The system utilizes pressure differentials in order to extract a processed medium sample from the process stream, as well as to convey along with a dilution medium the extracted sample to a mixing chamber. The sample and diluent are then mixed and conditioned for transfer to a measurement instrument for analysis.

The system of the present invention includes a source of a second pressure force connected to the mixing chamber, the second pressure force having a value less than the first pressure force of the process stream.

An extraction flow control device is connected to a probe and to a delivery conduit. The delivery conduit connects the mixing chamber and the second pressure force to the probe, which extends into the process stream. The extraction flow control device is operable into a first or alternatively a second position. With the extraction flow control device operated in the first position, the second pressure force is applied by the extraction flow control device to the probe. Responsive to the pressure force difference between the first pressure force and the second pressure force, a portion of the processed medium is drawn into the probe and is conveyed through the extraction flow control device to the delivery conduit, depositing therein the representative sample of the processed medium.

A source of diluent medium under a third pressure force is further included. The third pressure force has a value greater than the second pressure force. The source of diluent medium is also connected to the extraction flow control device. Operating the extraction flow control device into the second position isolates the first pressure force of the process stream from the second pressure force and connects the second pressure force to the third pressure force of the source of diluent medium. Responsive to the pressure force difference between the third pressure force and the second pressure force, diluent medium flows from the source of diluent medium through the extraction flow control device to the delivery conduit. The diluent medium flowing from the source and into the delivery conduit carries the representative sample previously deposited into the mixing chamber.

Accordingly, it is an object of the present invention to provide a system that overcomes the reliability problems of prior art systems and reduces maintenance of such systems by providing an extraction and delivery system that requires no mechanical extraction, motion arrangements, or seals to provide a diluted sample of a processed medium for measurement and analysis.

It is another object of the present invention to provide a system that uses pressure differentials controlled by flow control devices to extract and dilute a processed medium sample.

It is still another object of the present invention to provide an effective sampling and delivery system that can be used with any number of particle size distribution measurement instruments to effect the precise and cost-effective control of a processed medium.

BRIEF DESCRIPTION OF THE DRAWINGS

Other objects, features, and advantages of the present invention will be apparent from the following description of a preferred embodiment thereof, taken in conjunction with the single sheet of drawings showing in is a schematic block diagram view the sample extraction and diluting system in accordance to the concepts of the present invention.

DETAILED DESCRIPTION OF THE INVENTION

Turning to the single sheet of drawings, there is shown a sampling and diluting system for extracting and preparing a processed medium for analysis by a particle size distribution measurement instrument in accordance to the present invention. The system is comprised of an extraction arrangement that includes a pitot-like probe 10, inserted into a processed medium conveyed in a process stream within a conduit or pipe 80. Pipe 80 can either be a main conduit that transports the processed medium during a process operation or a by-pass line that shunts a portion of the processed medium from the main conduit. The processed medium flows within pipe 80 as a process stream in the direction shown by flow arrow F3. The probe 10 is also connected to an extraction flow control device 15. Extraction flow control device 15 is further connected to drive flow control device 20 via a conduit or tube 25. A sample delivery conduit 17 connects extraction flow control device 15 to a dilution or mixing chamber 30.

A dilution delivery arrangement includes a supply of clear diluent medium stored in a storage device 40 under a pressure greater than atmospheric pressure. It will be well understood by those skilled in the art that the dilution storage device may be supplied with diluent medium from a pressurized supply line. For example, if the diluent medium is clear water, diluent storage 40 can be connected to a water supply line. This water supply line would deliver the water to diluent storage 40 and also pressurize the tank due to the water supply line pressure. Diluent storage 40 is connected to mixing chamber 30 via a diluent delivery conduit 41. The flow and, therefore, introduction of diluent to mixing chamber 30 is controlled by diluent flow control device 45, located in conduit 41 between diluent storage 40 and mixing chamber 30. The diluent in storage device 40 is also connected via conduit 26 to drive flow control device 20.

Mixing chamber 30 is further connected via conduit 35 to a sampling chamber 51, located in the interior of a measurement or sampling cell 50. A probe 100 is operatively connected via a signal path 115 to a particle measurement instrument (not shown). The probe 100 is arranged to be installed in sampling cell 50 and to penetrate into chamber 51. The measurement instrument is a device of the type commonly used in particle size distribution measurement and analysis and that employs angular light scattering or dynamic light scattering techniques to measure particle size distribution. In such instruments a conditioned sample representing the processed medium is deposited in sampling chamber 51, whereby the measurement instrument performs the measurement and analysis on the conditioned sample contained in the sampling chamber. A better understanding of such an instrument and the method used for measurement and analysis may be had by reference to U.S. Pat. No. 5,416,580, to Trainer et al, issued May 16, 1995.

The sampling chamber 51 is further connected to drain flow control device 60 via a drain conduit 61. A circulating arrangement is also included comprising a circulation pump 70 having a first recirculation conduit 71 connected to pump 70 on one end and to drain conduit 61 on an opposite end. A second recirculation conduit 71 connects pump 70 to diluent delivery conduit 41. Flow control devices 20, 45 and 60 can be any manually adjustable valve, petcock or other such device that can be manipulated to alternatively open or close and control the flow of a medium through the conduits associated with each flow control device. Extraction flow control device 15 is a similar valve-like device; however, it is contemplated that device 15 can be manipulated to provide three distinct flow functions. It will be well understood by those skilled in the art that the conduits and their connections to the various components of the system just described can be made with any of the presently known methods for making pressure tight hydraulic or pneumatic closed loop systems employing either metal or plastic materials.

With renewed reference to the single sheet of drawings, an explanation of the operation of and the sequence of events required to initiate, extract, dilute and deliver a conditioned sample of the processed medium for measurement and analysis in accordance to the present invention, will now be given.

Before extraction of the sample from the process flow of pipe 80 is conducted, the mixing chamber is refreshed with diluent. This is accomplished by operating drain flow control device 60 to an open position. The open position provides a spill port and a low pressure port (0 gauge pressure, or atmospheric pressure) for the dilution delivery arrangement. Diluent flow control device 45 is then operated into an open position allowing the diluent stored in diluent storage 40, that is, under an operating pressure greater than the pressure at flow control device 60, to flow from diluent storage 40 into conduits 41, mixing chamber 30, conduit 35, sampling chamber 51, conduit 61 and out through flow control device 60 where it is drained away from the system. The circulating pump 70 may be also turned on to aid in the circulation of the diluent through mixing chamber 30, conduit 35 and sampling chamber 51. After a sufficient amount of time the diluent flow control device 45 is operated to the closed position, closing off the diluent in storage device 40 from the rest of the components associated with the diluent delivery arrangement. The drain flow control device 60, however, is left open for the next event in the operation.

This initial step or event flushes out any remaining processed medium sample left within the dilution delivery arrangement and sampling chamber 51 from a previous sample measurement. This step also fills the mixing chamber 30 and readies the dilution delivery arrangement for dilution and conditioning of the next sample to be measured.

The next event extracts a sample of the processed medium from the process stream flowing in pipe 80. As can be seen, probe end 10 is configured in pitot-tube like arrangement with the opening of the probe facing the process stream flowing in pipe 80. The impact of the process stream against the opening causes processed medium to enter the probe. A better understanding of the probe 10 and its operation may be had by reference to applicants co-pending U.S. patent application, Ser. No. 09/030,467, entitled, "A Sample Extraction Device For Minimizing Dead Volume", filed concurrently with the present invention and assigned to the same assignee and which is hereby incorporated by reference.

As was previously taught, extraction flow control device 15 is operable into three functional modes or positions. These modes place the flow control device into a closed, open to the process, or open to the diluent delivery system mode of operation. During the aforementioned initial event, flow control device 15 was in the closed position. In this extraction event the flow control device 15 is manipulated into the open to the process position. Concentrated processed medium contained in probe 10 is drawn past flow control device 15 into conduit 17. This is aided by the low pressure that is applied via flow control device 60. Flow control 60 being in the open position is open to a pressure that is lower than the supply pressure of the processed medium in pipe 80 and the impact pressure imparted by the process stream on the pitot opening of probe end 10. This causes a robust flow of concentrated processed medium to flow into conduit 17. The volume of concentrated processed medium extracted is dependent on the amount of time that the flow control device 15 is retained in the open to the process position.

When sufficient concentrated processed medium is extracted, the flow control device 15 is manipulated into the open to the diluent delivery system position. In this event the concentrated processed medium sample is driven to the mixing chamber for dilution and conditioning. The drain flow control device 60 is retained in the open position providing a low pressure port and the drive flow control device 20 is manipulated into the open position. With flow control device 20 in the open position, diluent under pressure from diluent storage device 40 flows through conduit 26 past flow control device 20 into conduit 25 and through flow control device 15, where it intercepts the concentrated processed medium contained in conduit 17. With the pressure being lower in conduit 35 due to flow control device 60 being open, the diluent flow through conduit 17 carries the extracted concentrated processed medium sample to mixing chamber 30. After a sufficient amount of time, drive flow control device 20 and flow control device 15 are closed.

In order to achieve a uniform mixing of the concentrated sample with the diluent medium, the diluent delivery arrangement is circulated via the circulation pump 70. This event mixes the concentrated sample delivered to the mixing chamber 30 with the diluent in chamber 30, thereby forming the diluted processed medium sample. The extracted sample is uniformly mixed in this event and delivered to the sampling chamber 51 for measurement and analysis. This event is effected by closing flow control device 60, forming a closed circulation loop between mixing chamber 30 and sampling chamber 51. Turning on pump 70, the diluted sample is drawn into conduit 35, through chamber 51 to conduit 61 and 71, through pump 70 into conduits 72 and 41, and back to mixing chamber 30. As will be well understood by those skilled in the art, the recirculation event just described, will obtain a uniform scattering of processed medium within the diluent contained now in the recirculation loop just described. Since the sampling chamber 51 is a part of this recirculation loop, a sample of the diluted sample remains in sampling chamber 51.

Dependent on which of the particle size distribution measurement techniques are used, i.e., dynamic light scattering or angular light scattering, the recirculating pump will remain on for a concentration measurement adjustment. The pump 70 is normally left on for angular light scattering measurements and turned off for dynamic light scattering. Probe 100 reads the sample in chamber 51 and passes the readings to the measurement instrument, where a loading or attenuation measurement is output by the instrument. This measurement ascertains if the diluted sample contained in chamber 51 is sufficiently conditioned to provide a reliable reading. If not enough processed medium is present in the conditioned sample, the extraction, delivery and recirculation events are repeated to obtain and introduce more concentrated processed medium to the diluent present in the system. If more diluent is required to further dilute the concentration, the initial or the delivery events are repeated for a short duration to introduce more diluent into the system. Once the concentration of the conditioned sample is found to be correct, a measurement reading is taken by the probe 100 of the sample contained in sampling chamber 51.

The system of the present invention overcomes the reliability problems of prior art systems and reduces maintenance of such systems by providing an extraction and delivery system that requires no mechanical extraction, motion arrangements, or seals to provide a diluted sample of a processed medium for measurement and analysis. Due to pressure differentials maintained within the system, only the manipulation of flow control devices is required to extract and dilute a processed medium sample. The magnitude of the dilution ratio is controlled by the volume of the dilution or mixing chamber and the time interval over which the concentrated process sample is drawn from the process into the system. Finally, the system of the present invention provides an effective and simple system that can be used with any number of particle size distribution measurement instruments to effect the precise and cost-effective control of a processed medium.

The present invention has been described with particular reference to the preferred embodiments thereof. It will be obvious that various changes and modifications can be made therein without departing from the spirit and scope of the invention as defined in the appended claims.

What is claimed is:

1. A system for the extraction of a representative sample of a processed medium, flowing in a process stream under a first pressure force, and the delivery of said extracted representative sample to a mixing chamber along with a diluent medium, said system comprising:

a source of a second pressure force connected to said mixing chamber, said second pressure force having a value less than said first pressure force;

an extraction flow control device connected to a probe and to a delivery conduit, said delivery conduit connected to said mixing chamber and said second pressure force and said probe extending into said process stream, said extraction flow control device operable into a first or alternatively a second position and in said first position said second pressure force is applied by said extraction flow control device to said probe and responsive to the pressure force difference between said first pressure force and said second pressure force, a portion of said processed medium flows through said probe and is conveyed through said extraction flow control device to said delivery conduit, depositing therein said representative sample; and a source of diluent medium under a third pressure force, said third pressure force having a value greater than said second pressure force and said source of diluent medium connected to said extraction flow control device, and wherein when said extraction flow control device is operated into said second position, said first pressure force is isolated from said second pressure force and said second pressure force is connected to said third pressure force, whereby responsive to the pressure force difference between said third pressure force and said second pressure force, diluent medium flows from said source of diluent medium through said extraction flow control device to said delivery conduit, conveying said representative sample and diluent medium to said mixing chamber.

2. The system as claimed in claim 1 wherein said source of diluent medium is a diluent storage vessel containing said diluent medium therein, said diluent medium is stored in said storage vessel under said third pressure force.

3. The system as claimed in claim 2 wherein said extraction flow control device is further operable into a third position, wherein said first pressure force is isolated from said second pressure force and said third pressure force is isolated from said second pressure force, said system further includes a diluent delivery conduit connected from said diluent storage vessel to said mixing chamber, said diluent delivery conduit including a diluent flow control device operable into a first or alternatively a second position, and responsive to said extraction flow control device operated into said third position, said diluent flow control device is operated into said first position connecting said third pressure force to said second pressure force, whereby diluent medium flows from said diluent storage vessel to said mixing chamber through said diluent delivery conduit and said diluent flow control device.

4. The system as claimed in claim 3 wherein said mixing chamber includes an outlet conduit and said system further includes a sampling cell operatively connected to a measurement instrument, said sampling cell connected to said outlet conduit and to said source of second pressure force whereby said second pressure force is applied to said mixing chamber through said sampling cell and said outlet conduit.

5. The system as claimed in claim 4, wherein said system further includes a drain conduit connected to said sampling cell and a drain flow control device connected to said drain conduit and to said source of said second pressure force, said drain flow control device operable into a first or alternatively a second position, and said drain flow control device is operated into said first position to connect said source of second pressure force to said drain conduit and to said sampling cell, whereby said second pressure force is applied to said mixing chamber through said sampling cell and said outlet conduit.

6. The system as claimed in claim 5, wherein said system further includes a recirculation arrangement connecting said drain conduit to said diluent delivery conduit through a pump device, wherein responsive to said drain flow control device operated into said second position, said second pressure force is isolated from said mixing chamber, and said diluent flow control device is operated in said second position isolating said third pressure force from said mixing chamber, said pump device is energized, conducting the contents of said mixing chamber through said sampling cell and back to said mixing chamber, whereby said representative sample is dispersed within said diluent medium, forming a diluted representative sample that is conveyed by said recirculation arrangement to said sampling cell for measurement and analysis by said measurement instrument.

7. The system as claimed in claim 5, wherein said source of said second pressure force is the surrounding air pressure at the normal sensed air pressure above sea level where the system is operated.

8. The system as claimed in claim 7, wherein said process stream flows in a conduit and said process stream flows under a flow pressure that has a value greater than the surrounding air pressure where the system is operated defining said first pressure force.

9. The system as claimed in claim 7, wherein said diluent medium stored in said diluent storage vessel is pressurized with an internal pressure force that has a value greater than the surrounding air pressure where the system is operated.

10. A system for the extraction of a representative sample of a processed medium, flowing in a process stream under a first pressure force, and the delivery of said extracted representative sample to a mixing chamber along with a diluent medium, said system comprising:

a source of a second pressure force connected to said mixing chamber, said second pressure force having a value less than said first pressure force;

means for extracting said processed medium connected to said mixing chamber and to said process stream, said means for extracting operable into a first or alternatively a second position, and in said first position said means for extracting connects said second pressure force to said process stream, and responsive to the pressure force difference between said first pressure force and said second pressure force, a representative sample of said processed medium is conveyed from said processed stream through said means for extraction; and means for providing said diluent medium under a third pressure force, said third pressure force having a value greater than said second pressure force, said means for providing said diluent medium connected to said means for extracting, and wherein when said means for extracting is operated into said second position, said first pressure force is isolated from said second pressure force, and said second pressure force is connected to said third pressure force, whereby responsive to the pressure force difference between said third pressure force and said second pressure force, said diluent medium flows through said means for extracting driving said representative sample along with said diluent medium to said mixing chamber.

* * * * *